United States Patent [19]

Kraemer

[11] Patent Number: 5,585,608

[45] Date of Patent: Dec. 17, 1996

[54] OPERATING HANDLE INCLUDING SWITCHES AND PRESSURE SENSORS FOR MEDICAL EQUIPMENT

[75] Inventor: Rainer Kraemer, Fuerth, Germany

[73] Assignee: Siemens Aktiengesellschaft, Munich, Germany

[21] Appl. No.: 393,822

[22] Filed: Feb. 24, 1995

[30]    Foreign Application Priority Data

Mar. 10, 1994 [DE] Germany .......................... 44 08 128.6

[51] Int. Cl.$^6$ .............................. H01H 9/06; A61B 19/00
[52] U.S. Cl. ...................................................... 200/61.85
[58] Field of Search ............................ 200/52 R, 17 R,
   200/6 A, 61.85 R–61.91, 293.1–307, 329;
   74/144–149, 471 XY; 338/99, 114

[56]            References Cited

U.S. PATENT DOCUMENTS

| | | | |
|---|---|---|---|
| 3,260,826 | 7/1966 | Johnson | 200/61.85 |
| 3,723,687 | 3/1973 | Adkinson | 200/6 A X |
| 3,867,600 | 2/1975 | Phillips | 200/293.1 |
| 4,587,471 | 5/1986 | Barthelmes et al. | 318/628 |
| 4,650,172 | 3/1987 | Wathlet | 5/601 |
| 4,962,448 | 10/1990 | DeMario et al. | 200/6 A X |
| 4,965,939 | 10/1990 | Hans | 33/558 |
| 5,007,300 | 4/1991 | Siva | 74/471 X |
| 5,033,324 | 7/1991 | Glaser | 200/61.88 X |

FOREIGN PATENT DOCUMENTS

| | | | |
|---|---|---|---|
| 0346503 | 6/1988 | European Pat. Off. | B25S 13/02 |
| 3009496 | 5/1982 | Germany | A61B 6/00 |
| 4218019 | 9/1993 | Germany | A61B 6/00 |
| 4230048 | 1/1994 | Germany | A61B 6/00 |

OTHER PUBLICATIONS

Patents Abstracts of Japan, M–1442, Jul. 9, 1993, vol. 17/365, Japanese App. 3–223056.

*Primary Examiner*—J. R. Scott
*Attorney, Agent, or Firm*—Hill, Steadman & Simpson

[57]            ABSTRACT

A gripping member of an operating handle is adjustable via a holder around a rotational axis aligned substantially perpendicularly relative to its longitudinal axis, with the rotational axis being in the middle region of the gripping member. In a further version, the gripping member is adjustable via a holder around a swiveling axis that intersects an axis aligned substantially perpendicularly relative to the longitudinal axis of the gripping member with the rotational axis lying in the middle of the gripping member. Finger operated switches are located on the gripping member and various pressure sensors are activated dependent upon the movement of the gripping member and its holder about relevant axes.

10 Claims, 2 Drawing Sheets

OPERATING HANDLE INCLUDING SWITCHES AND PRESSURE SENSORS FOR MEDICAL EQUIPMENT

BACKGROUND OF THE INVENTION

1. Field of the Invention

The present invention is directed to an operating handle for moving a relatively heavy apparatus, such as a medical device, the handle being of the type having a gripping member that, by means of a holder, is adjustable around a rotational axis aligned substantially perpendicularly relative to its longitudinal axis.

The invention is also directed to an operating handle for moving a relatively heavy apparatus, such as a medical device, the handle being of the type having a gripping member that, by means of a holder, is adjustable around a swiveling axis that intersects an axis aligned substantially perpendicularly relative to the longitudinal axis of the operating handle.

2. Description Of the Prior Art

Medical systems such as x-ray therapy and diagnostics installations have a number of relatively heavy components which must be positioned by a physician or an attendant relative to the examination subject, or relative to other components, in a manner which varies with each treatment or examination. Such components may be mounted on a wall or a ceiling of the installation room such as by means of a parallelogram arrangement. In some installations, the movement of the components is undertaken completely by physical exertion on the part of the physician or attendant, in other systems once a small force has been exerted on the component in a particular direction, the actual movement of the component is taken over by motor control.

German OS 30 09 496 discloses a medical apparatus in the form of an x-ray target device wherein a command arm is adjustable around its longitudinal axis. Switch keys for controlling the apparatus are provided in the middle region of the command arm.

In an x-ray target device disclosed in German OS 42 18 019, a rod-shaped handle is held at a distance from the x-ray target device via a holder and is held pivotable around an axis parallel to its longitudinal axis.

German OS 30 048 discloses another x-ray target device. An operating handle thereof is L-shaped and is seated at one side of the x-ray target device by means of a first leg. A gripping member of the operating handle, forming a second leg, is held at the side so as to be adjustable around the longitudinal axis of the first leg, which is oriented approximately perpendicularly to the longitudinal axis thereof. Switch means for controlling components are provided at the second leg. Further, the second leg is adjustable around a swiveling axis that intersects an axis that is aligned substantially perpendicularly relative to the longitudinal axis of the gripping member.

SUMMARY OF THE INVENTION

An object of the present invention is to provide an operating handle for a medical device of the type initially generally described which improves the manipulation of the medical device via the operating handle. Another object is to provide such an operating handle which allows fatigue-free operation and manipulation for operators who differ in size. In particular, a comfortable and simple adjustment of a medical device such as an x-ray target device should be ergonomically achieved.

The above object is achieved in accordance with the principles of the present invention in an operating handle attached to a relatively heavy component, such as a component of a medical apparatus, wherein the operating handle has a gripping member which, by means of a holder, is adjustable around a rotationally axis which is oriented substantially perpendicularly relative to a longitudinal axis of the gripping member, with the rotational axis being disposed in a middle region of the gripping member.

An advantage of the invention is that the operating handle is adjustable around a rotary axis that lies in the middle of the gripping member. An adjustment of the operating handle around this rotary axis can thus ensue torque-compensated (equalized). When this operating handle is utilized in an x-ray target device, a simple and comfortable operation is also possible when the x-ray target device is adjusted, for example, from a horizontal into a vertical position.

The above object is also achieved in an operating handle having a gripping member which, by means of a holder, is adjustable around a swiveling axis which intersects a further axis which is oriented substantially perpendicularly to the longitudinal axis of the gripping member, with the further axis being disposed in a middle region of said gripping member.

An advantage of this version is that the operating handle is adjustable around a swiveling axis that lies on an axis arranged in the middle of the operating handle. A swiveling of the operating handle is thereby possible with low torque. Moreover, the operating handle can be swiveled into a position wherein easy operation is possible for persons who differ in size.

It is especially advantageous when the operating handle is adjustable both around the rotational axis and around the swivelling axis. The operating handle can thus be adjusted into a position which is optimum for operation by rotation and swiveling given all apparatus positions.

DESCRIPTION OF THE PREFERRED EMBODIMENTS

Figure 1:
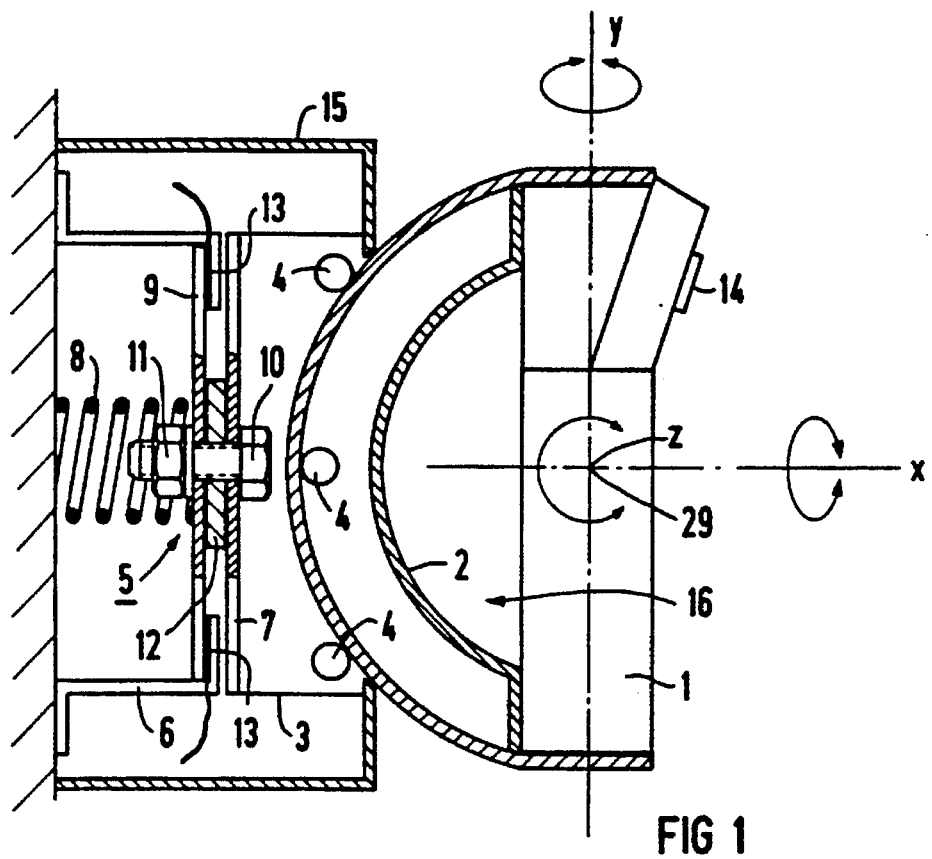
FIG. 1 illustrates an operating handle of the invention in a side sectiona view.
Figure 2:
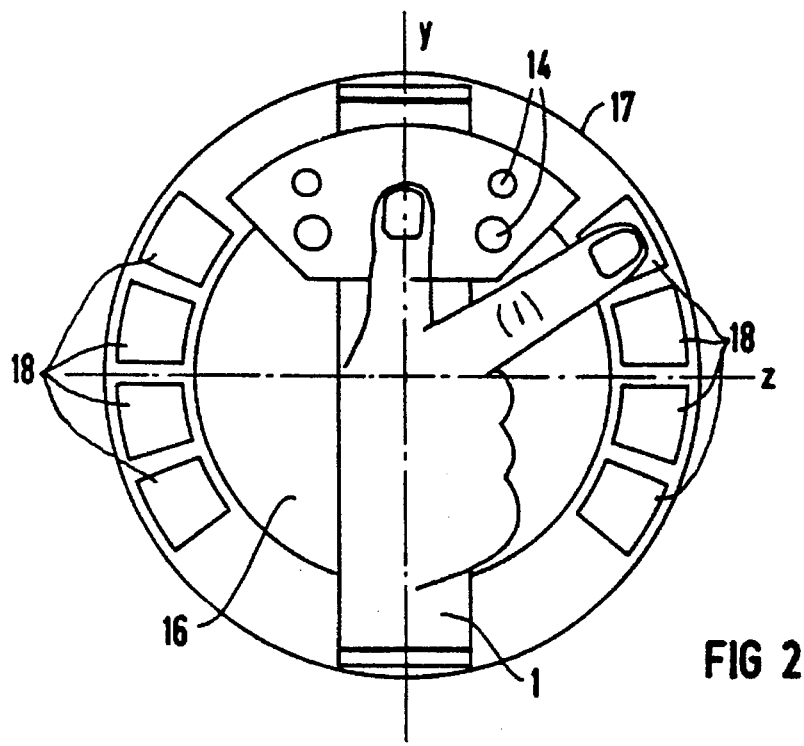
FIG. 2 illustrates the operating handle of FIG. 1 in a plan view.

FIG. 1 shows a side view of a preferred embodiment of an operating handle of the invention. The handle has C-shaped arcuate part 2 which embraces a rod-shaped gripping member 1. The C-shaped part 2 is adjustable within a bearing 3 along its circumference, for which purpose three roller bearings 4 are preferably provided. These roller bearings 4 are arranged such that at least two roller bearings 4 attack at a first surface and at least one roller bearing 4 attacks at the opposite surface of the C-shaped part 2. It is advantageous when at least one roller bearing 4 is adjustable-for example, via an eccentric-in the direction toward the allocated surface, so that the pressing power of the roller bearing 4 against the surfaces, and thus the bearing play, can thereby be set. Alternatively, however, a spring/lever arrangement can be employed. An advantage of this three-point bearing in conjunction with the roller bearings 4 is a high pressing power given low rolling friction and little play, so that an easy and play-free adjustment of the C-shaped part 2 along its circumference is possible. The gripping member 1 is adjustable around a swiveling axis z that intersects a rotational axis x, and aligned substantially perpendicularly relative to the longitudinal axis y of the gripping member 1. The z and x axes preferably intersect the y axis at a middle region, such as the mid-point, along the longitudinal (y-axis) length of the gripping member i.e., at is middle. Preferably, the longitudinal axis y, the swiveling axis z and the rotational axis x are aligned perpendicularly relative to one another.

A frame 6 is provided for attaching the overall assembly shown in FIG. 1 to a device to be manipulated, such as a medical device. A pivot bearing 5 is arranged between the bearing 3 and the frame 6 for adjusting the gripping member I around the rotational axis x. For fashioning the pivot bearing 5, a recess is provided in the center of a bottom plate 7 of the bearing 3 and in the center of a plate 9 supported at the frame 6 by the power of a spring 8. A screw 10 that is secured by a nut 11 extends, for example, through this recess. In order to keep the frictional forces given an adjustment of the gripping member I around the rotational axis x as low as possible, a glide washer 12 having a low coefficient of friction is arranged between the bottom plate 7 and the plate 9. The glide washer 12 can, for example, be composed of Teflon® or of polyamide. The size of the glide washer 12 is dimensioned such that a force from the gripping member 1 is precisely transmitted onto the plate 9 and tilting is avoided.

At least one sensor 13 is preferably provided between the plate 9 and the frame serving as pressure pick-up; the signal therefrom can be evaluated by an evaluation unit (not shown) and can be utilized for controlling a component of the medical device. It is especially advantageous when at least four sensors 13 are utilized for this purpose, these being implemented as pressure-dependent resistors, for example in the form of semiconductor polymer foils or wire strain gauges, and being arranged, for example, at corners of the plate 9.

A tilting of the plate 9 ensues when a force is applied to the gripping member 1 in a selected direction. Due to a change in pressure, this tilting effects a change in resistance of at least one sensor 13 that can be acquired by the evaluation unit. On the basis of the signal of the at least one sensor 13, the evaluation unit produces an output signal that is supplied to one or more drives, such as motor drives, for assisting the adjustment of, for example, an x-ray target device in the spatial directions. The x-ray target device is thus adjustable into the desired direction by applying a slight force to the gripping member 1, assisted by the drives.

It is advantageous within the scope of the invention for the gripping member 1 to be held by the C-shaped part 2 so as to be adjustable around its longitudinal axis y. The adjusting force can thereby be set via the coefficients of friction between the C-shaped part 2 and the end faces of the gripping member 1 and by making the the length of the gripping member I longer than the distance between the ends of the C-shaped part 2.

Due to the adjustability of the gripping member 1 around the swiveling axis z, the longitudinal axis y and the rotational axis x, the gripping member I can be adjusted into a position favorable for operation.

Switch elements 14 with which the functions of the medical device can be triggered can be provided at the gripping member 1. The switch elements 14 can be implemented, for example, as a key field and are preferably arranged such at the gripping member 1 such that they can be actuated with the thumb and without a change in position of the hand at the gripping member I being necessary for this purpose. The keys are preferably arranged at different levels dependent on the value to be set or on the function to be triggered thereby, and are arranged symmetrically relative to a center axis. Comfortable operation both for left-handed as well as for right-handed persons is possible due to the symmetrical arrangement of the keys relative to the center axis. The key field is preferably manufactured of one-piece silicone on which function symbols of the keys are applied. Such a fashioning is economical in terms of manufacture; moreover, it can be cleaned in a simple way and thus meets hygienic requirements. The line connections from the switch elements 14 to an evaluation unit are thereby preferably guided in the C-shaped part 2 that, for example, is fashioned as a curved, metallic tube hollow for this purpose. The line connections, however, can alternatively be accepted in a C-shaped part 2 manufactured of plastic and reinforced with a steel clip.

As shown in FIGS. I and 2, the bearing 3 and the frame 6 are surrounded by a cap 15 such that a gripping opening 16 in the form of a spherical segment arises. The cap 15 is adjustable around the rotational axis x together with the gripping member 1 and, in a further embodiment, has an edge 17 outside the gripping opening 16 at which further switch elements 18 for triggering functions of the medical device are arranged. These further switch elements 18 are arranged at the edge 17 such that, for example, they can be actuated with the fingers of the hand without having to move the hand from the gripping member 1.

Figure 3:
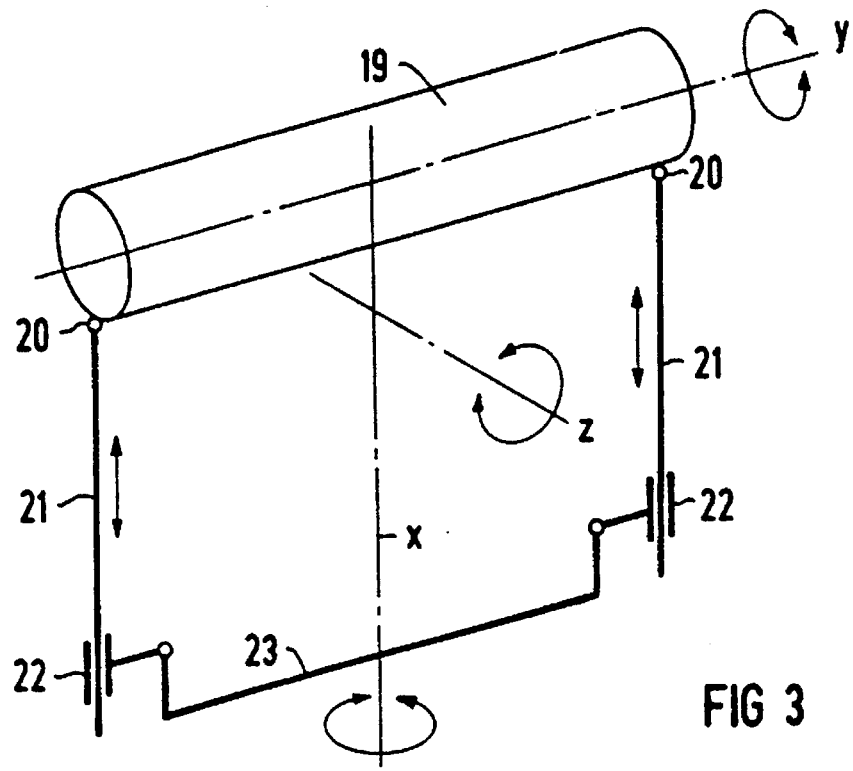
FIG. 3 is a schematic illustration of an embodiment of the operating handle of the invention wherein the gripping member is held at its opposite ends.

In the further exemplary embodiment of an operating handle of the invention which is shown only schematically in FIG. 3, a gripping member 19 is held at its end by bearings that form an articulation 20 with respective rods 21 attached to the articulations 20. The rods 21 are adjustable, for example, in bushings or longitudinal guides 22 that are provided at a bearing 23. The gripping member 19 is thus adjustable around the swiveling axis z. The bearing 23 can also enable an adjustment of the gripping member 19 around the rotational axis x.

Figure 4:
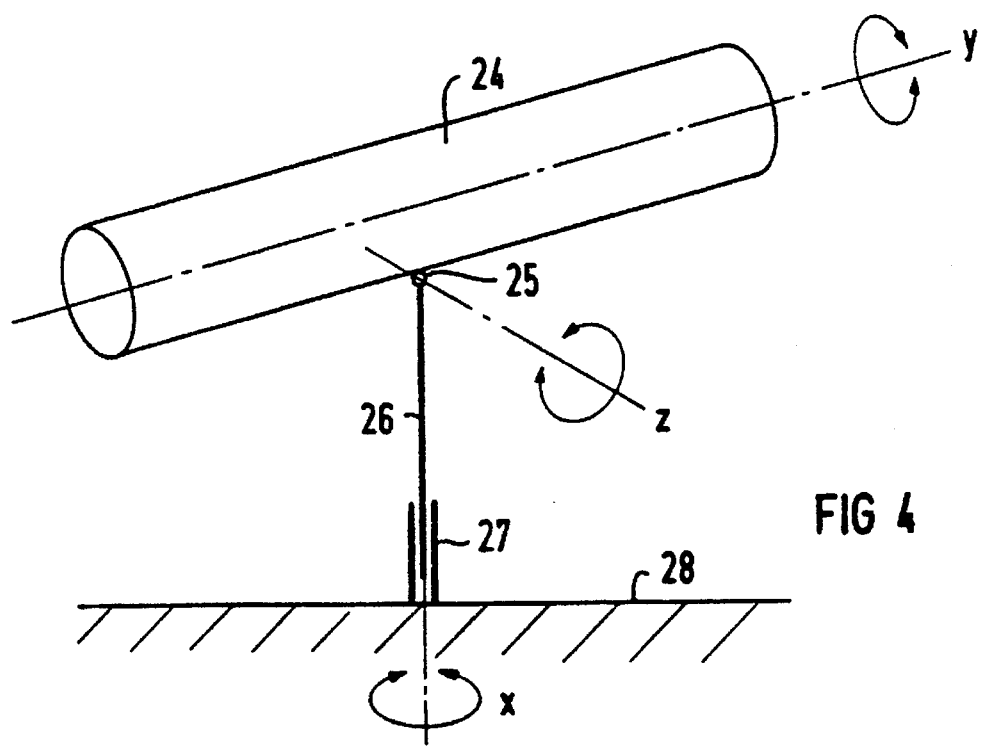
FIG. 4 is a schematic illustration of an embodiment of an operating handle of the invention wherein the gripping member is mounted for adjustment around a central swiveling axis.

In the further exemplary embodiment of an operating handle of the invention shown only schematically in FIG. 4, a bearing 25 that allows an adjustment of the gripping member 24 around the swiveling axis z is provided approximately centrally at the gripping member 24. A rod 26 that is adjustable in a pivot bearing 27 of a bearing 28 attacks at the bearing 25. The gripping member 24 can thus be adjusted around the rotational axis x.

Within the scope of the invention, the gripping members 19 and 24 can also be seated adjustable around their longitudinal axis.

It is advantageous given the operating handles of the invention to fashion the gripping members 1, 19 and 24 such that the center of the hand assumes a position when grasping the gripping member 1, 19 and 24 such that the hand preferably lies in the pivot point 29 of the operating handle. The pivot point 29 can thereby preferably lie in the intersection of the rotational axis x, the longitudinal axis y and the swiveling axis z. Particularly in the first exemplary embodiment, the pivot point 29 can lie in the center of gravity formed by the C-shaped part 2 and by the gripping member 1 or can lie in the geometric center of the C-shaped part 2. The operating force thus acts in the intersection of all three axes of the operating handle, so that a low-friction, mass-compensated bearing, and thus a substantially torque-free adjustment, in the adjustment directions is achieved.

Although modifications and changes may be suggested by those skilled in the art, it is the intention of the inventor to embody within the patent warranted hereon all changes and modifications as reasonably and properly come within the scope of his contribution to the art.

I claim as my invention:

1. An operating handle for moving a heavy device, comprising:

a gripping member, having a longitudinal axis, graspable by a hand; and holder means, attached to said gripping member and adapted for attachment to said device, for adjusting a position of said gripping member around a rotational axis disposed substantially perpendicularly to said longitudinal axis, said rotational axis being disposed in a middle region of said gripping member, said holder means comprising a C-shaped arcuate part attached to said gripping member and having a circumference, and bearing means acting on said circumference for permitting movement of said C-shaped arcuate part along said circumference, a plate to which said bearing means are attached, a frame adapted for attachment to said device, a spring disposed between said device and said plate for biasing said plate against said frame, and pressure sensor means disposed between said plate against said frame for generating electrical signals corresponding to forces applied to said gripping member.

2. An operating handle as claimed in claim 1 wherein C-shaped arcuate part and said gripping member, in combination, have a center of gravity and wherein said swiveling axis and said rotational axis intersect substantially at said center of gravity.

3. An operating handle as claimed in claim 1 wherein C-shaped arcuate part and said gripping member, in combination, have a geometric center and wherein said swiveling axis and said rotational axis intersect substantially at said geometric center.

4. An operating handle as claimed in claim 1 wherein said gripping member is attached to said C-shaped arcuate part by attachment means for permitting rotation of said gripping member around said longitudinal axis.

5. An operating handle as claimed in claim 1 wherein said plate has a plurality of corners, and wherein said pressure sensor means comprise a plurality of pressure-dependent resistors respectively disposed at said corners of said plate.

6. An operating handle as claimed in claim 1 wherein bearing means are rotatable around said rotational axis, and said operating handle further comprising switch means for operating said device disposed at said bearing.

7. An operating handle as claimed in claim 1 further comprising switching means for operating said device disposed at said gripping member.

8. An operating handle as claimed in claim 7 wherein said gripping member has a plurality of different levels and wherein said switching means comprises a plurality of switching elements, said switching elements being respectively disposed at said different levels of said gripping member.

9. An operating handle as claimed in claim 1 wherein said holder means comprises means for permitting rotation of said gripping member around said longitudinal axis.

10. An operating handle as claimed in claim 1 further comprising a plurality of manually actuatable elements disposed on said holder means symmetrically relative to said longitudinal axis of said gripping member.

* * * * *